US006355048B1

(12) United States Patent
Hong et al.

(10) Patent No.: US 6,355,048 B1
(45) Date of Patent: Mar. 12, 2002

(54) SPHERICAL LINKAGE APPARATUS

(75) Inventors: Boyang Hong, Oakdale; Arthur G. Erdman, New Brighton, both of MN (US)

(73) Assignee: GeoDigm Corporation, Chanhassen, MN (US)

( * ) Notice: Subject to any disclaimer, the term of this patent is extended or adjusted under 35 U.S.C. 154(b) by 0 days.

(21) Appl. No.: 09/426,298

(22) Filed: Oct. 25, 1999

(51) Int. Cl.$^7$ ................................................ A61B 19/00

(52) U.S. Cl. ........................................ 606/130; 606/107

(58) Field of Search ................................ 600/236, 235, 600/233, 229, 228; 606/130, 107

(56) References Cited

U.S. PATENT DOCUMENTS

| | | | |
|---|---|---|---|
| 4,997,369 A | | 3/1991 | Shafir |
| 5,017,139 A | | 5/1991 | Mushabac |
| 5,050,608 A | * | 9/1991 | Watanabe et al. ............ 606/130 |
| 5,078,140 A | * | 1/1992 | Kwoh ......................... 606/130 |
| 5,131,844 A | | 7/1992 | Marinaccio et al. |
| 5,697,939 A | * | 12/1997 | Kubota et al. ............... 606/130 |
| 5,762,458 A | * | 6/1998 | Wang et al. .................. 606/130 |
| 5,810,765 A | * | 9/1998 | Oda ............................. 606/107 |
| 5,824,007 A | * | 10/1998 | Faraz et al. .................. 606/130 |
| 5,847,528 A | * | 12/1998 | Hui et al. ................. 318/568.1 |
| 5,891,034 A | * | 4/1999 | Bucholz ....................... 606/130 |
| 5,891,157 A | * | 4/1999 | Day et al. .................... 606/130 |
| 5,971,997 A | * | 10/1999 | Guthrie ........................ 606/130 |

OTHER PUBLICATIONS

Gosselin et al., "On the Development of the Agile Eye," *IEEE Robotics & Automation Magazine*, pp. 29–37 (Dec. 1996).

Ham et al., "Spherical Four–Bar Linkage Mechanism for Continuous Passive Movement Rehabilitation Treatment of the Ankle," *Proceedings of The 1996 ASME Design Engineering Technical Conferences and Computers in Engineering Conference*, pp. 1–6 (Aug. 18–22, 1996).

Hong et al., "Design of Adjustable Spherical Four–Bar Linkages as Continuous Passive Motion Devices for Anatomic Joints Rehabilitation," *Proceedings of The 1996 ASME Design Engineering Technical Conferences and Computers in Engineering Conference*, pp. 1–10 (Aug. 18–22, 1996).

Merkle, R., New Positional Device, "A New Family of Six Degree of Freedom Positional Devices," *http://www.zyvex.com/nanotech/6dofhtml*, , pp. 1–12 (Printed Sep. 14, 2001).

Merlet, Parallel manipulators: state of the art and perspectives, *http://wwwsop.inria.fr/saga/personnel/merlet/Etat/etat_de_lart.html*, pp. 1–9 (Printed May 18, 1999).

(List continued on next page.)

*Primary Examiner*—Paul J. Hirsch
(74) *Attorney, Agent, or Firm*—Merchant & Gould PC

(57) ABSTRACT

A five bar spherical serial closed loop linkage includes a first link, and a second link rotatably mounted to the first link about a first axis of rotation, the axis of rotation passing through a center of a sphere defined by the linkage. A third link rotatably mounts to the second link about a second axis of rotation passing through the center of the sphere. A fourth link rotatably mounts to the third link about a third axis of rotation passing through the center of the sphere. A fifth link rotatably mounts to the fourth link about a fourth axis of rotation passing through the sphere's center, and rotatably mounts to the first link about a fifth axis of rotation passing through the center of the sphere. An instrument mounts to the linkage and typically is aligned with the spherical center. Two motors having encoders drive the two degrees of freedom and are in communication with a central processor or controller to control movement of the linkage.

24 Claims, 3 Drawing Sheets

OTHER PUBLICATIONS

"Kinematics and dynamics of parallel mechanisms and manipulators", *http://wwwrobot.gmc.ulaval.ca/*, pp. 1–10 (Printed May 18, 1999).

Dec. 1996 Robotics and Automation Index and Abstracts, *http://www.ncsu.edu/IEEERAS/RAM/RAMissues/RAMissues/RAMvol03no04.html*, pp. 1–3 (Printed May 18, 1999).

* cited by examiner

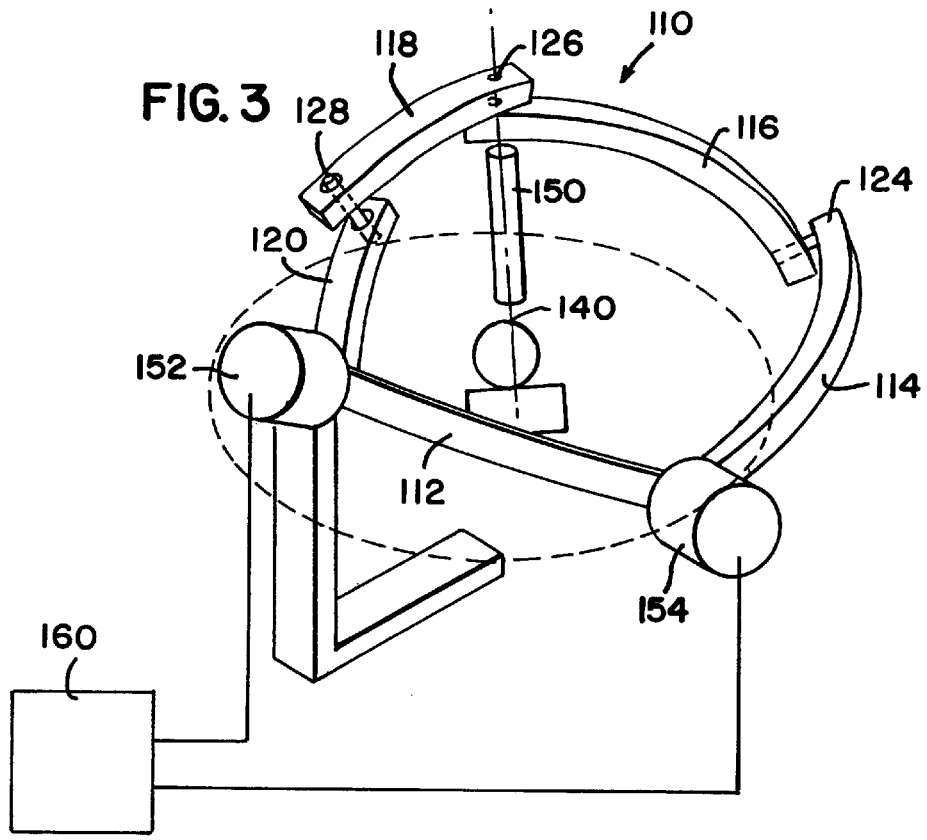
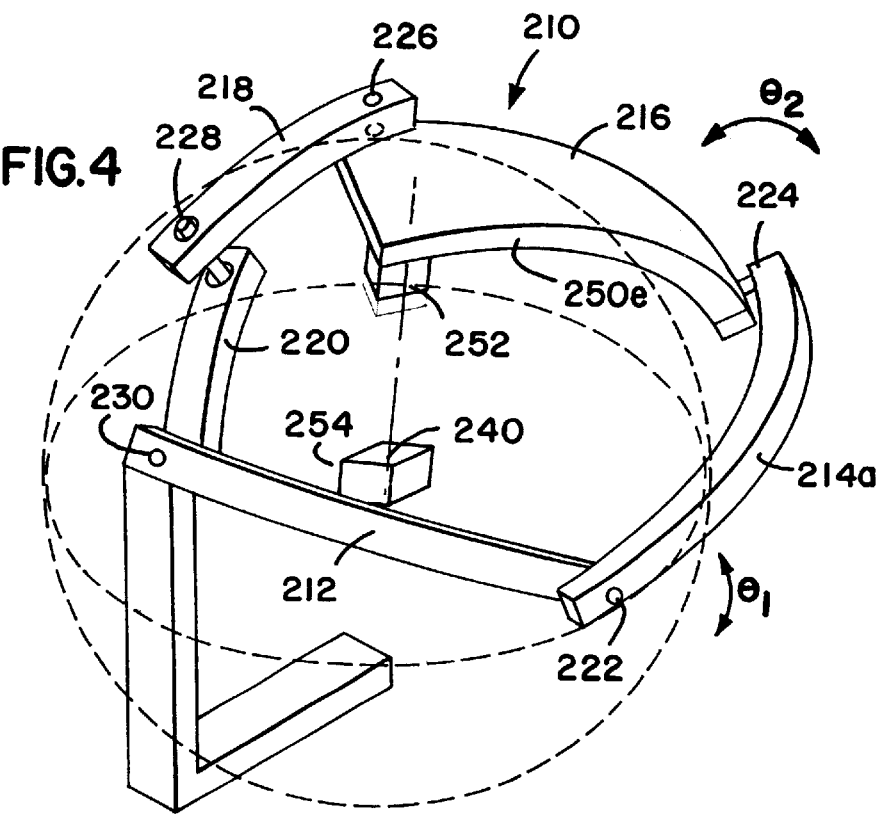

SPHERICAL LINKAGE APPARATUS

BACKGROUND OF THE INVENTION

1. Field of the Invention

The present invention is directed to a spherical linkage, and in particular to a closed loop serial spherical linkage having five interconnected links.

2. Prior Art

Multiple link linkages for moving devices along paths of motion with or without orientation are well known, and may have four, five or more links. Such devices may be used for a number of different functions and are used to move elements through paths of motion, typically around one or more pivots.

Serial type linkages are often used in digitizing applications, to move a device at an extended end of the linkage. Such linkages typically have the various link members connected in an end-to-end relationship, but have an open loop rather than a closed loop. Therefore, such linkages are prone to more imprecision than closed loop linkages due to tolerances building up from the base to the extended end. Although such devices provide great flexibility, each link provides an additional degree of freedom which requires an additional driver, one for controlling each degree of freedom to provide the necessary control at the extended end of the linkage. As more drivers are required for the linkage, the mass of the linkage is increased so that movement is more difficult due to greater inertia. Therefor, the linkage must be designed with a greater load capacity than would otherwise be required.

The imprecision is compounded as the additional drivers which provide control may each add some imprecision associated with stopping the motor at a desired location. Control of such a linkage is difficult as the multiple degrees of freedom must be coordinated for accurate usage. Although such devices may be useful for some applications, they have drawbacks which limit their usage in many applications.

A spherical linkage has been developed for uses such as for rehabilitation of the ankle. Such a device is described in the article entitled "Spherical Four-Bar Linkage Mechanism for Continuous Passive Movement Rehabilitation Treatment of the Ankle" presented at the 1996 American Society of Mechanical Engineers Design Engineering Technical Conference in Computers and Engineering Technical Conferences and Computers and Engineering Conference from Aug. 18–22, 1996, in Irvine, Calif. The device provides for moving the patient's ankle in a continuous motion and provides a closed loop linkage. The closed spherical design provides improved support over open serial type linkages. However, the four bar spherical linkage does not provide sufficient degrees of freedom to provide for other paths of motion which may be required with many applications. The linkage can only trace one path of motion for any instrument or device mounted thereon.

Heretofore, devices using spherical linkages of more than four bars have taken the form of parallel linkages, wherein links are connected to one another but not in a serial configuration. An example of such a parallel type linkage is the Agile Eye, developed to support photography and having extremely fast reaction times. The Agile Eye is capable of making adjustments much faster than the human eye. Although the Agile Eye obtains great speeds for changing camera angles, it has a limited range of motion, limiting the camera range. The Agile Eye requires a complicated parallel arrangement with the links nesting within one another. Moreover, the equations defining and controlling parallel linkages are more complicated and difficult to solve than the equations for serial linkages.

It can be seen then that a spherical five-bar closed loop linkage is required which overcomes the shortcomings of the linkages of the prior art. Such a linkage should provide precision and support through a closed loop linkage. In addition, the linkage should provide multiple degrees of freedom and a range of motion which accommodates multiple functions requiring multiple paths of motion. The linkage should also provide movement of devices relative to one another. The linkage should provide for manipulating instruments to access the interior of the sphere defined by the linkage. The present invention addresses these as well as other problems associated with the prior art.

SUMMARY OF THE INVENTION

The present invention is directed to a linkage apparatus, and in particular to a spherical five bar closed loop serial linkage. The linkage may be utilized in systems for scanning, surgical procedures, and other applications requiring precise motion.

The spherical linkage defines a sphere having a center through which the axis of rotation through a first joint passes. In addition, the axes of rotation of all the joints between the various links also pass through the same spherical center. The respective lengths, radiuses and angles of the various links may be varied, but each axis of rotation will always intersect with the center of the sphere defined by the linkage. The linkage includes a first link, designated as a ground link having a first end pivotally connected to a first end of a second link. The second end of the second link connects to the first end of the third link at a second joint having an axis of rotation extending through the intersection at the center of the linkage sphere. The second end of the third link connects to the first end of a fourth link through a third joint having an axis of rotation also intersecting at the center of the sphere. The second end of the fourth link connects to a first end of a fifth link to a fourth joint having an axis rotation extending through the center of the sphere. The second end of the fifth link and the second end of the first or ground link connect at a fifth joint having an axis of rotation extending through the center of the sphere.

The lengths of the various links and radius may be varied. Each link is defined by an angular measurement between the two axis of rotations originating at the center of the linkage sphere. For example, a link may be designated as an 80° link. As the radius is decreased or increased, the linkage is still operable with that link defining the same angle. The combinations of the various angles will define the rotational ranges for the various angles. For example, with some embodiments, one or more links are able to rotate 360°, while in some embodiments, no link will be able to rotate 360°.

The spherical serial closed loop five bar linkage has two degrees of freedom. Therefor, devices utilizing the linkage include two drive motors to position the various links. The drivers may be positioned at adjacent joints or spaced apart, depending on the particular application.

In one application, the linkage is utilized in a scanning device for scanning and digitizing objects. A scanner is positioned apart from the linkage and an object placed within the linkage sphere proximate the center. The spherical linkage provides for moving the scanner and object being scanned relative to one another without the linkage interfering with the scanning beam. For example, dental scanning may be accomplished with the linkage of the present invention. A supported dental mold is passed through the scanner beam at various angles, creating a digital model of the mold.

In another application, the linkage is utilized for supporting instruments for surgery performed on the eye. The linkage of the present inventions allows for making a small puncture at a single point on the surface of the eyeball coinciding with the spherical center of the linkage. In this manner, the instrument extending through the spherical center may be moved through the fluid making up the interior of the eye without creating a tear or larger opening at the surface of the eye.

Other applications may also be utilized that employ non-linear paths of motions along three axes. The linkage of the present invention may be used in other biological and industrial applications suited for linkages that interact with spherical or curved shapes, such as scanning and digitizing objects. A spherical closed loop five bar linkage provides greater strength and support with less flexure than serial open linkages. In addition, a supported instrument may be offset from its supporting link to provide improved access without interference with other links, objects or a scanning beam. The spherical linkage has multiple configurations and link combinations to meet the needs and parameters, of the particular application.

These features of novelty and various other advantages which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

Referring now to the drawings, wherein like reference numerals and letters indicate corresponding structure throughout the several views:

FIG. 3 shows a perspective view of a linkage according to the principles of the present invention having a first device mounted thereto;

FIG. 4 shows a perspective view of a linkage according to the principles of the present invention having a second device mounted thereto.

DETAILED DESCRIPTION OF THE PREFERRED EMBODIMENT(S)

Figure 2:
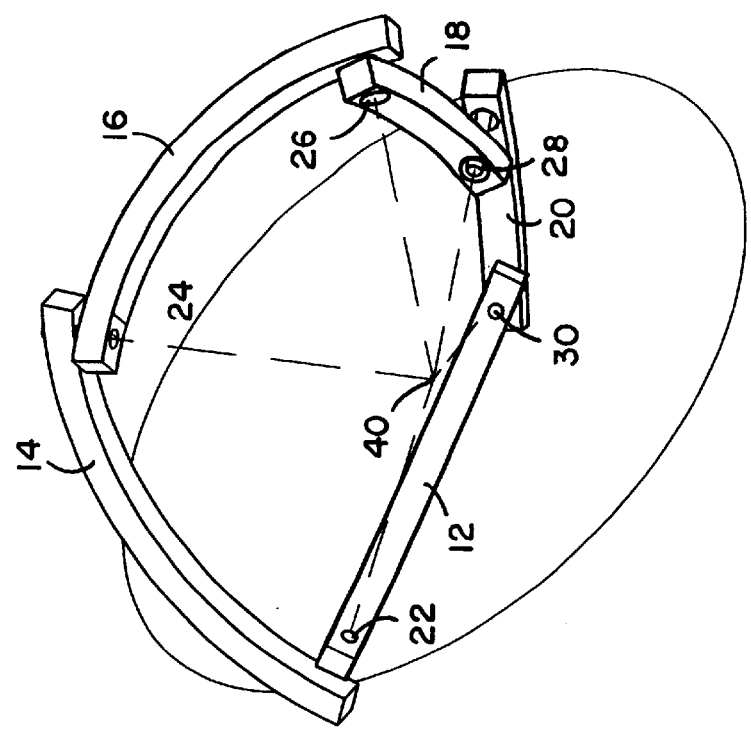
FIG. 2 shows a perspective view of the linkage of FIG. 1 in a second position.
Figure 1:
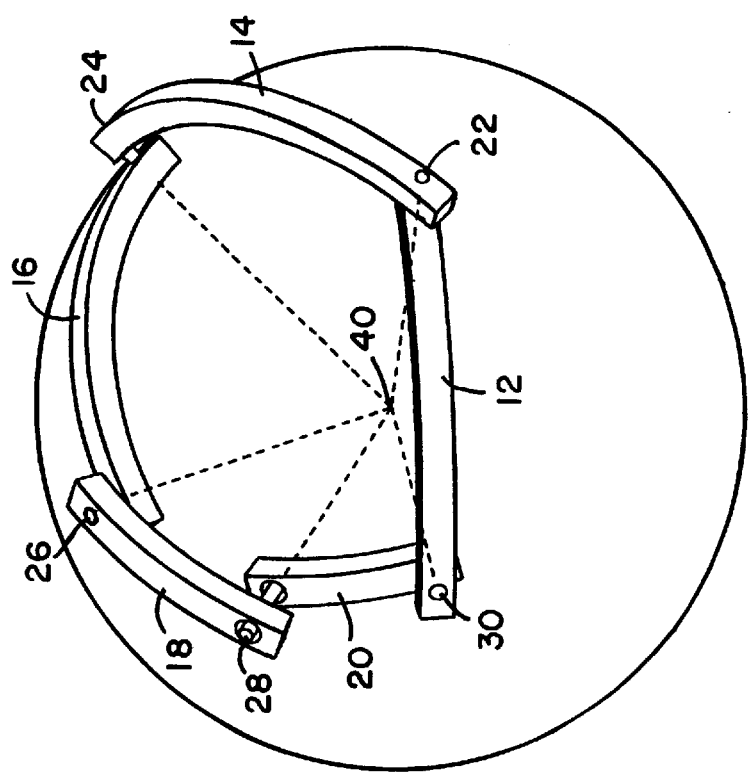
FIG. 1 shows a perspective view of closed loop serial linkage according to the principles of the present invention.

Referring to the drawings, and in particular to FIGS. 1 and 2, there is shown a spherical five bar linkage, generally designated 10. The linkage 10 extends a around a spherical center 40, as explained hereinafter, and includes five links pivotally connected together in a serial arrangement. The five bar spherical linkages prescribes that the axes passing through the joints at which the links are connected all intersect at the spherical center 40.

The spherical linkage 10 includes a first link 12 designated as the ground link. However, it will be appreciated that any of the other links could be designated as the ground link with the other links moved relative to that link. The linkage 10 is shown only as an example, of one of many possible link and angle combinations. Other links and angles may be utilized, as prescribed by the requirements for each use. The first link 12 pivotally connects at a first end to a first end of a second link 14 about a first joint 22. The rotational axis of the first joint 22 always passes through the spherical center 40 at all positions of the linkage 10. The second link 14 is connected at a second end to a first end of a third link 16 about a second joint 24. The rotational axis of the second joint 24 also intersects the spherical center 40. As the linkage 10 moves through various positions, the rotational axes between links may move, but are always aligned to intersect the spherical center 40. The third link 16 is pivotally connected at a second end to a first end of a fourth link 18. The third and fourth links 16 and 18 joint relative to one another about a third joint 26. The rotational axis of the third joint 26 also passes through the spherical center 40 and intersects the spherical center 40 at all positions. The fourth link 18 is pivotally connected at a second end to a fifth link 20. The fourth and fifth links 18 and 20 are pivotally connected about a fourth joint 28 that has a rotational axis that always passes through the spherical center 40. The fifth link 20 is connected at its second end to the first ground link 12. The first link 12 and fifth link 20 are pivotally connected about a fifth joint 30 that has an axis which always passes through the spherical center 40.

As the five bar linkage 10 includes two degrees of freedom, there are two drivers to move the linkage to its various positions and to maintain the linkage 10 at any desired position. The drivers may typically be mounted to either the first or fifth joints 22 or 30 of the ground link 12 to minimize the mass being moved. However, one or more of the drivers may be mounted at any of the other joints to drive the various links relative to one another. As long as there are two inputs to the linkage 10, for its two degrees of freedom, the position and motion of any link may be controlled. As the linkage 10 is a closed loop linkage, it provides more stability than open serial linkages, as there is no open ended link with a non-supported end, as occurred in prior gimbal type devices.

Figure 5:
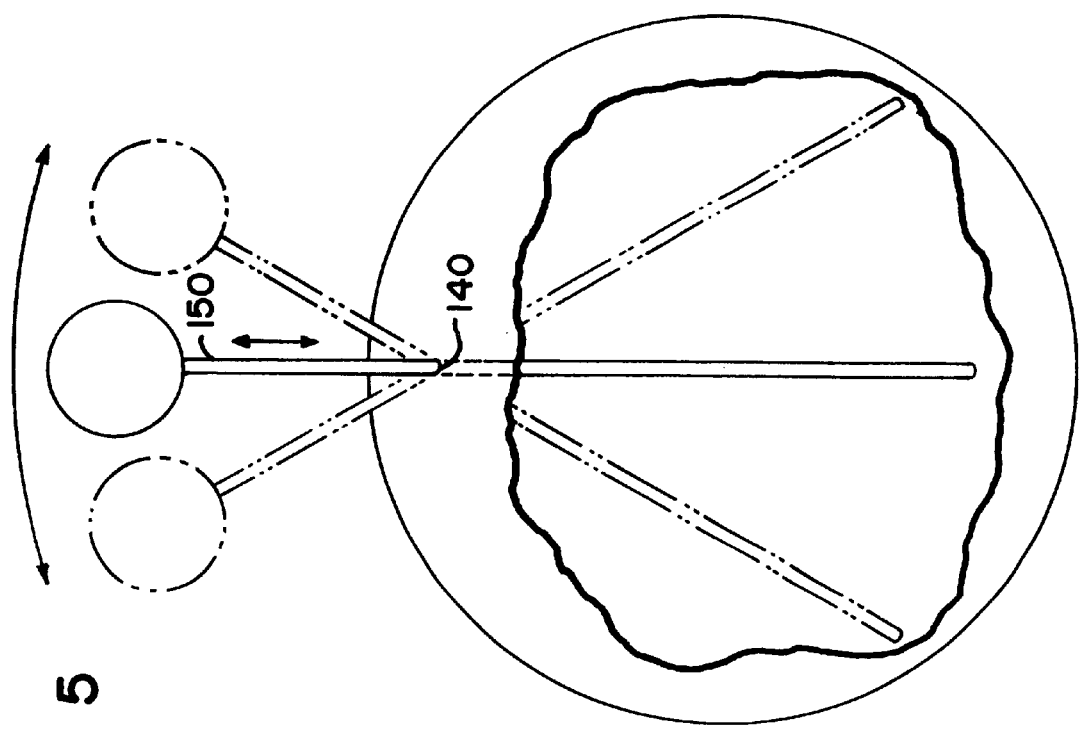
FIG. 5 shows a perspective view of the device of FIG. 3 with the center of the spherical linkage coinciding with an entry point on the surface of an object.

Referring now to FIG. 3, a second embodiment has a linkage 110 such as may be used in an eye surgery system. It can be appreciated that a first link 112 of a second embodiment may be supported on a base, shown as an L-shaped section, to provide clearance to the other links as the linkage 110 moves through its various positions. The spherical linkage 110 includes links 112, 114, 116, 118 and 120 pivotally connected in a serial arrangement. A particular application of the linkage 110 supports a probe or other instrument 150 for surgery. A spherical center 140 of the linkage 110 is aligned with a point on the surface of the eyeball, as also shown in FIG. 5. The surgical instrument 150 may be extended into the eyeball at that location, requiring only a tiny hole. A large incision or tear is not required for accessing the interior of the eye with an end of the instrument 150, as is required with other devices. As the linkage 110 moves the instrument 150, it will continuously extend through the spherical center 140 at the single entry point on the surface of the eye. In the embodiment shown, the linkage has the instrument 150 mounted to the third and fourth links and passing through the center 140 which is aligned with the entry point on the surface of an eye, as shown in FIG. 5. In a preferred embodiment, the instrument 150 is controllably extendible and retractable through the entry point. In addition, two drivers 152 and 154 drive the linkage 110 to position it in at a desired position and through desired paths of motion. The drivers 152 and 154 are typically micro-stepper motors or servo motors that include encoders and are in communication with a central processor or controller 160 to coordinate and control motion of the linkage 110. The precision needed for such an application is very high. In the preferred embodiment, each joint is a precision needle bearing assembly with the rotational axis directed through the spherical center 140. An alignment device 156, such as a head clamp, may be utilized to maintain alignment between the spherical center and the entry point. Although the apparatus 110 is shown used for eye surgery, it may be used for any application in which it is desired to minimize the size of the entry point, while still providing movement of the instrument beyond the entry point.

Turning now to FIG. 4, there is shown another embodiment such as may be used for a mechanical digitizer. A digitizer device 244, includes a linkage 210 having a first link 212 connected to a second link 214 at the first end. The second link 214 connects at its second end to a first end of a third link 216. The second end of the third link pivotally connects to a first end of a fourth link 218. The second end of the fourth link 218 pivotally connects to a first end of a fifth link 220. The second end of the fifth link 220 pivotally connects back to a second end of the first link 212. The first rotational axis 222 extends between the first and second link and through the spherical center 240 while a second rotational axis extends 224 through the intersection of the joint between the second and third links and also extends through the spherical center 240. A third rotational axis 226 extends through the joint between the third link 216 and the fourth link 218 while a fourth rotational axis 228 extends through the joint between the fourth link 218 and the fifth link 220. Finally, a fifth rotational axis 230 extends through the joint between the fifth link 220 and the first link 212. All of the joint rotational axes 222, 224, 226, 228 and 230 intersect at the spherical center 240. The scanner apparatus 252 may also include a widened offset portion 250 including a scanner or other instrument or tool 252 extending inwardly directed at the spherical center 240. A holder device 254 positions the scanned object at or near the spherical center 240. As with the embodiment shown in FIG. 2, the linkage 200 includes two drivers, each having an encoder. In addition, an encoder is generally positioned at a joint of the link on which the scanner 252 is mounted. Although encoders are placed at the other two joints in some applications, they are redundant and not needed with the serial closed loop design. Such simplification decreases costs for the scanner. However, including encoders at all joints increases the accuracy of the control of the system.

Each of the links can be represented by the angle between the rotational axes passing through the two joints associated with the link. For example, links may be designated as a 30° degree link or a 90° degree link. This angle does not vary as the linkage is activated or the radius of a link from the spherical center is changed.

It has been found that having a 90-degree link connected to a 90 degree link provides advantages at certain applications for a apparatus in maximum work space. Such a linkage 210 is shown in FIG. 4 and includes 90 degree link 214 and a 90 degree offset portion 250. The rotational axes of the joints all extend through the spherical center 240. With either two 90-degree links, or a 90 degree link and a 90 degree offset, the trace of an instrument supported on the linkage 210 covers a complete sphere.

To quantify the maximum work space available for any linkage design, a spherical work space index (SWSI) is utilized and provides quantification for the motion available for any particular five bar spherical closed loop linkage, providing a new approach for calculating spherical workspace. As illustrated in FIG. 4, the workspace of the scanner 252 can be calculated by investigating spherical serial arm 214 (a in the calculations below) and link 250 (e in the calculations below). The consequence of link 212, link 220, and link 218 is to restrict the range of rotation of axis 222, angle $\theta_1$ and axis 224, angle $\theta_2$. The SWSI can be calculated, building on the calculation of the range of motion of $\theta_1$ and $\theta_2$. The mathematical formula used to calculate the spherical work space index is quite complicated and must be broken down into several groups:

EXAMPLE 1

Both link "a" and link "e" can rotate 360 degrees.

$$SWSI=\pi[\sin^2(a+e)+(1-\cos(a+e))^2]-\pi[\sin^2(a-e)+(1-\cos(a-e))^2]$$

EXAMPLE 2

Link "a" can rotate 360 degrees and Link "e" is limited between $\beta_{min}$ and $\beta_{max}$ and e1 is defined as the projection of link e to link a, when the rotation angle is $\beta_{max}$, and e2 is defined as the projection of link e to link a, when the rotation angle is $\beta_{min}$. According to spherical trigonometry, $$\frac{\tan(e1)}{\tan(e)} = \cos(180 - \beta_{max}) = -\cos(\beta_{max})$$

$$e1 = \tan^{-1}(-\cos(\beta_{max}) \cdot \tan(e))$$

$$\frac{\tan(e2)}{\tan(e)} = \cos(\beta_{min})$$

$$e2 = \tan^{-1}(\cos(\beta_{min}) \cdot \tan(e))$$

The calculation of SWSI is as follows:

$$SWSI=\pi[\sin^2(a+e1)+(1-\cos(a+e1))^2]-\pi\cdot[\sin^2(a-e2)+(1-\cos(a-e2))^2](4.22)$$

EXAMPLE 3

Link "a" is limited between $\alpha_{min}$ and $\alpha_{max}$, Link "e" can rotate 360 degrees $$SWSI = \pi \cdot [\sin^2(e) + (1 - \cos(e))^2] +$$
$$\pi \cdot \frac{\alpha_{max} - \alpha_{min}}{360} [\sin^2(a+e) + (1 - \cos(a+e))^2] -$$
$$\pi \cdot [\sin^2(a-e) + (1 - \cos(a-e))^2]$$

EXAMPLE 4

Both $\alpha$ and $\beta$ have limited range of motion.

$$SWSI = \frac{\alpha_{max} - \alpha_{min}}{360} \{\pi \cdot [\sin^2(a+e1) + (1 - \cos)a - e1))^2] -$$
$$\pi \cdot [\sin^2(a-e2) + (1 - \cos(a-e2))^2]\}$$

Even though two adjacent 90-degree links are necessary to create a maximum workspace, in the actual design, only one link needs to be 90 degree. The other 90-degree link is embedded to the edge of the offset 250, shown in FIG. 4. This design provides at least two advantages:

(1) It gives a designer extra flexibility to select the mounting location for end-effector, such as scanner 252 in FIG. 4. The end-effector does not need to mount to a joint axis. This gives a designer additional freedom to avoid potential interference of the scanner with other components on the actual design.

(2) Designers also have freedom to select the link length of the four non-90 degree links. A new simple method is created for the selection of link length to ensure the two input angles can fully rotate 360 degrees. This method is described as follows:

The method to determine the rotatability of the only one input angle within a spherical four bar linkage is well known. It is called Grashof's rule.

To determine the rotatability of the first input angle in the spherical five bar linkage, the following step is applied:

Hold the second input angle to be 0 degree and 180 degree. The five bar linkage becomes a four-bar linkage. If the first input angle can fully rotate 360 in the above formed four bar linkage, the first input angle can fully rotate in the five bar linkage.

To determine the rotatability of the second input angle, the following step is applied:

Hold the first input angle to be 0 degree and 180 degree. The five bar linkage becomes a four-bar linkage. If the second input angle can fully rotate 360 degree in the above formed four bar linkage, the second input angle can fully rotate in the five bar linkage.

Using these formulas and principles to calculate ranges of motion and areas of ranges of motion, appropriate linkages may be designed to meet design requirements and optimize various parameters.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A spherical closed loop serial linkage, comprising:
   a first link;
   a second link pivotally mounted to the first link about a first axis;
   a third link pivotally mounted to the second link about a second axis;
   a fourth link pivotally mounted to the third link about a third axis;
   a fifth link pivotally mounted to the fourth link about a fourth axis and pivotally mounted to the first link about a fifth axis;
   wherein the first axis, second axis, third axis, fourth axis, and fifth axis extend through an intersection.

2. A linkage according to claim 1, wherein the linkage has at least two degrees of freedom.

3. A linkage according to claim 1, further comprising a first driver connected to a first one of the links.

4. A linkage according to claim 3, further comprising a second driver connected to a second one of the links.

5. A linkage according to claim 1, wherein the intersection is positioned inside a sphere defined by the links.

6. A linkage according to claim 5, further comprising an encoder mounted with each of the first and second drivers.

7. A linkage according to claim 1, wherein each of the first, second, third, fourth, and fifth axes of rotation comprises a revolute joint.

8. A linkage according to claim 1, wherein the pivotal mounts comprise single axis rotational joints.

9. A linkage according to claim 1, wherein the linkage traces a range of motion covering a sphere.

10. A linkage according to claim 1, wherein at least one of the links comprises a 90 degree link, and wherein the linkage includes a second 90 degree link or a 90 degree offset.

11. A linkage according to claim 6, wherein the first and second drivers and encoders are in communication with a controller for controlling and coordinating linkage position and movement.

12. A linkage according to claim 11, wherein two of the joints comprises non-encoder joints.

13. A linkage according to claim 11, wherein all of the joints include encoders.

14. A five bar closed loop serial linkage, comprising:
    a first link;
    a second link rotatably mounted to the first link about a first axis of rotation; the axis of rotation passing through an intersection;
    a third link rotatably mounted to the second link about a second axis of rotation passing through the intersection;
    a fourth link rotatably mounted to the third link about a third axis of rotation passing through the intersection;
    a fifth link rotatably mounted to the fourth link about a fourth axis of rotation passing through the intersection, and rotatably mounted to the first link about a fifth axis of rotation about a fifth axis of rotation.

15. A linkage according to claim 14, further comprising a first drive and a second drive.

16. A linkage according to claim 15, wherein the first and second drives are located at adjacent links.

17. A five bar spherical serial linkage apparatus, comprising:
    a first link;
    a second link rotatably mounted to the first link about a first axis of rotation; the axis of rotation passing through an intersection;
    a third link rotatably mounted to the second link about a second axis of rotation passing through the intersection;
    a fourth link rotatably mounted to the third link about a third axis of rotation passing through the intersection;
    a fifth link rotatably mounted to the fourth link about a fourth axis of rotation passing through the intersection, and rotatably mounted to the first link about a fifth axis of rotation passing through the intersection; and
    an instrument mounted to the linkage and having a portion of the instrument proximate the intersection.

18. A linkage according to claim 17, wherein the spherical linkage comprises a spherical serial five bar closed loop linkage.

19. A linkage according to claim 17, wherein the spherical linkage comprises two motors for driving the linkage.

20. A linkage apparatus according to claim 17, wherein the instrument comprises an eye surgical instrument and includes an alignment device for locating the spherical center at the surface of the eye.

21. A linkage according to claim 17, wherein the instrument is extendible and retractable through the intersection.

22. A linkage according to claim 17, wherein the instrument comprises a scanner scanning an object substantially at the spherical center.

23. A method of providing entry of a device into an object through a single entry point, comprising the steps of:

providing a five bar spherical closed loop serial linkage have a spherical center;

locating the spherical center of the linkage at a desired entry point on the object;

mounting the device on the linkage aligned with the spherical center;

extending the device to the entry point.

24. A method according to claim 23, wherein the device comprises a surgical instrument and wherein the object comprises an eye, whereby the spherical center is aligned with an entry point on the surface of the eye.

* * * * *